United States Patent
Nazareth et al.

(10) Patent No.: US 10,101,342 B2
(45) Date of Patent: Oct. 16, 2018

(54) DEVICES AND METHODS FOR ELECTRONIC ANALYTE ASSAYING

(71) Applicant: CHURCH & DWIGHT CO., INC., Princeton, NJ (US)

(72) Inventors: Albert R. Nazareth, Mercerville, NJ (US); Benedict Zin, San Diego, CA (US); Andy Sturman, San Diego, CA (US); Shang Li, West Windsor, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 1103 days.

(21) Appl. No.: 14/178,672

(22) Filed: Feb. 12, 2014

(65) Prior Publication Data
US 2015/0226752 A1   Aug. 13, 2015

(51) Int. Cl.
*G01N 21/00*   (2006.01)
*G01N 33/76*   (2006.01)
*G01N 33/543*   (2006.01)

(52) U.S. Cl.
CPC ....... *G01N 33/76* (2013.01); *G01N 33/54366* (2013.01)

(58) Field of Classification Search
CPC .................................................. G01N 21/00
USPC ..... 422/50, 68.1, 82.05, 82.09; 436/43, 164; 702/19, 22, 23, 30, 32
See application file for complete search history.

(56) References Cited

U.S. PATENT DOCUMENTS

| | | |
|---|---|---|
| 6,136,610 A * | 10/2000 | Polito et al. ................... 436/514 |
| 6,847,451 B2 | 1/2005 | Pugh |
| 6,940,598 B2 | 9/2005 | Christel et al. |
| 7,214,542 B2 | 5/2007 | Hutchinson |
| 7,220,597 B2 | 5/2007 | Zin et al. |
| 7,254,503 B2 | 8/2007 | Howard, III |
| 7,283,245 B2 | 10/2007 | Xiao et al. |
| 7,768,645 B2 | 8/2010 | Roman |
| 8,128,871 B2 | 3/2012 | Petruno et al. |
| 8,153,081 B2 | 4/2012 | Kuriger |
| 8,231,832 B2 | 7/2012 | Zanzucchi et al. |
| 8,247,233 B2 | 8/2012 | Gofman et al. |
| 2004/0043502 A1* | 3/2004 | Song et al. ................... 436/172 |
| 2004/0151632 A1* | 8/2004 | Badley et al. .............. 422/82.08 |
| 2006/0240541 A1* | 10/2006 | Petruno et al. ............. 435/287.2 |
| 2010/0206055 A1* | 8/2010 | Abbott et al. ............... 73/53.01 |
| 2011/0223673 A1 | 9/2011 | Profitt |
| 2012/0282636 A1* | 11/2012 | Altschul et al. ............. 435/7.92 |

(Continued)

FOREIGN PATENT DOCUMENTS

WO   2010071708 A1   6/2010

*Primary Examiner* — Brian J Sines
(74) *Attorney, Agent, or Firm* — Church & Dwight Co., Inc.

(57) ABSTRACT

An improved qualitative or semi-quantitative diagnostic test for measuring low levels of any analyte, such as hCG, in a biological sample, such as urine. The test comprises a test device containing reagents for the detection of the monitored analyte and an electronic reader that measures color development at a detection area of the device. The color development is converted to an electronic or digital signal. Improvements were made to the electronic reader to optimize the coverage of the detection area on the test strip. This improves the detection sensitivity and consistency of the test result while maintaining its reliability and accuracy.

15 Claims, 6 Drawing Sheets

(56) References Cited

U.S. PATENT DOCUMENTS

2013/0065321 A1    3/2013   Nazareth
2013/0137940 A1*   5/2013   Schafer .................. 600/301

* cited by examiner

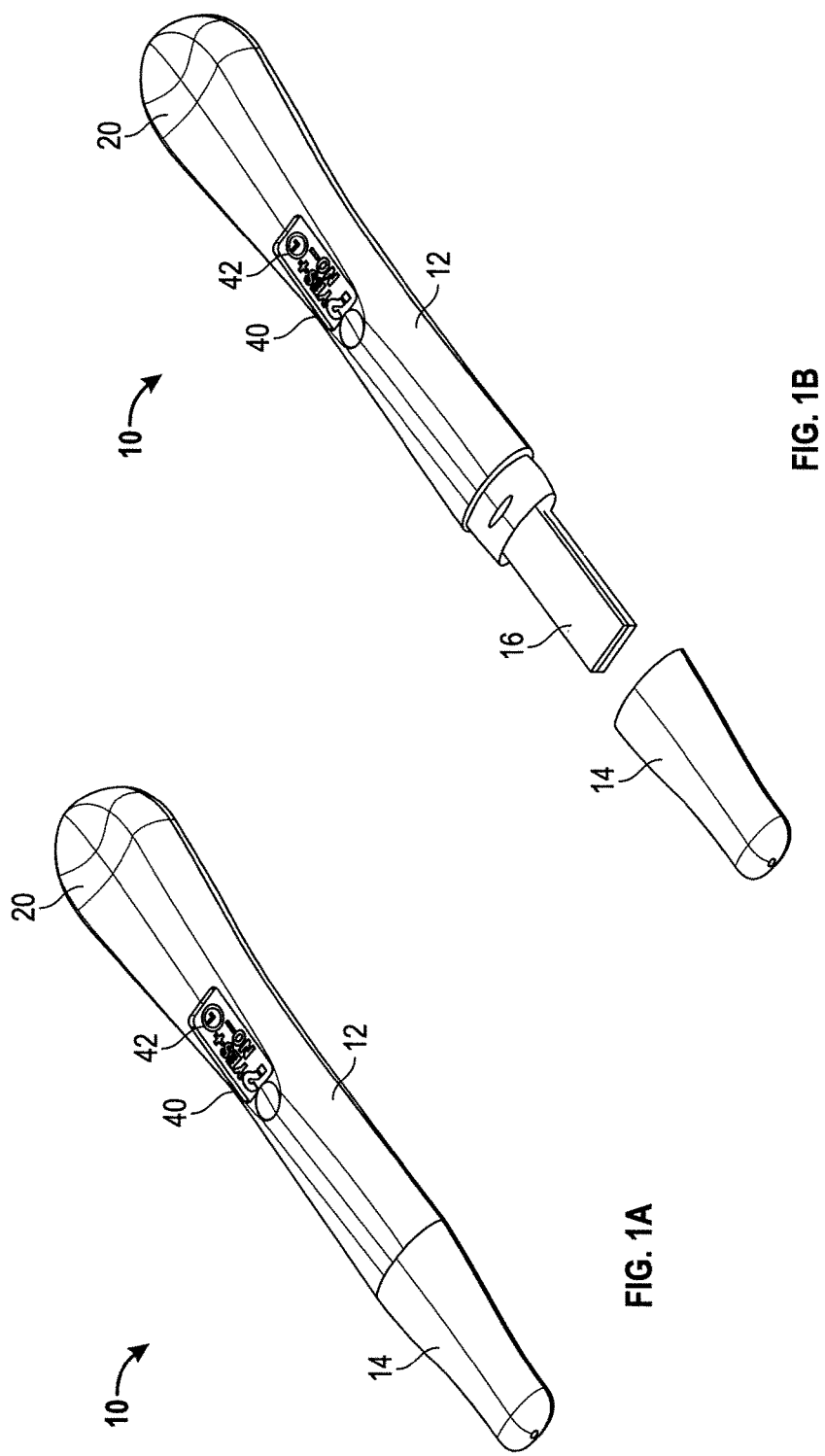

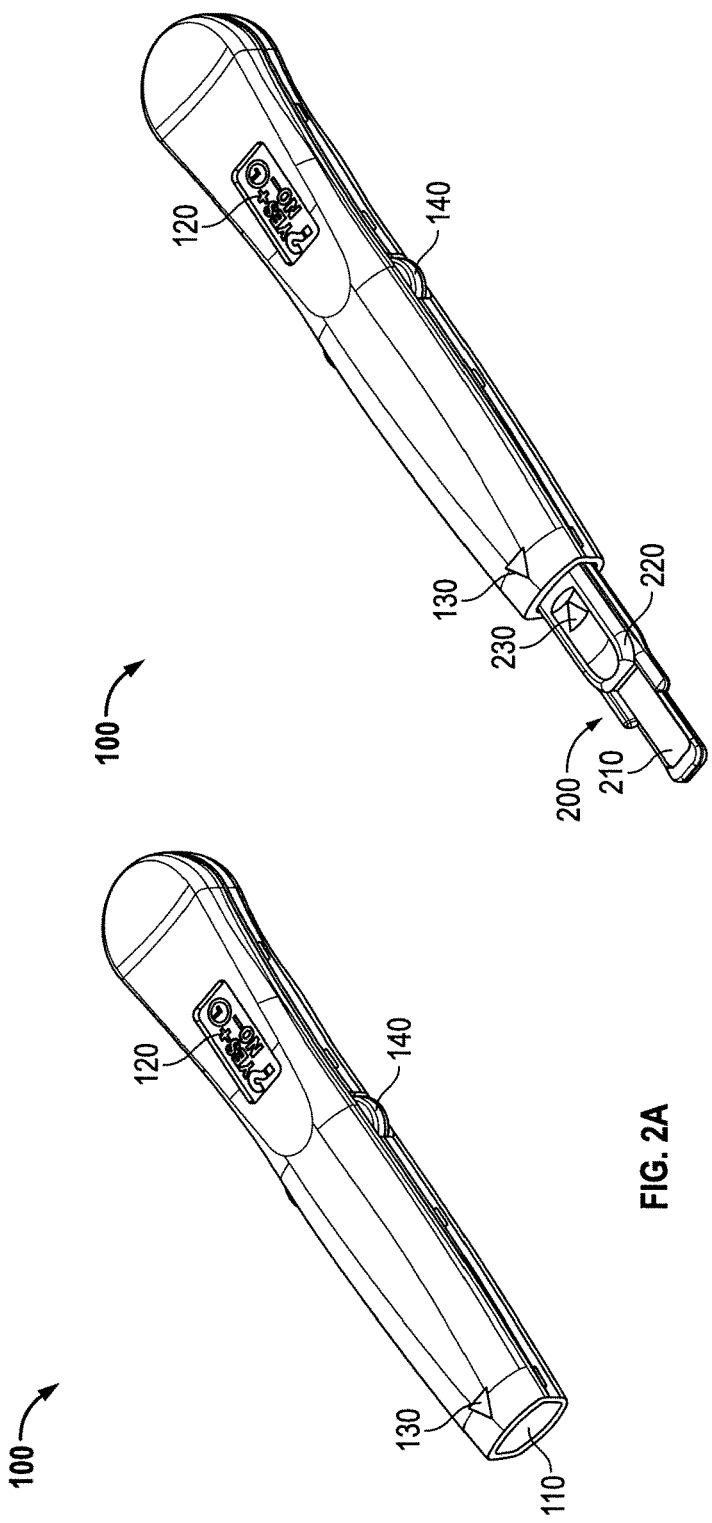

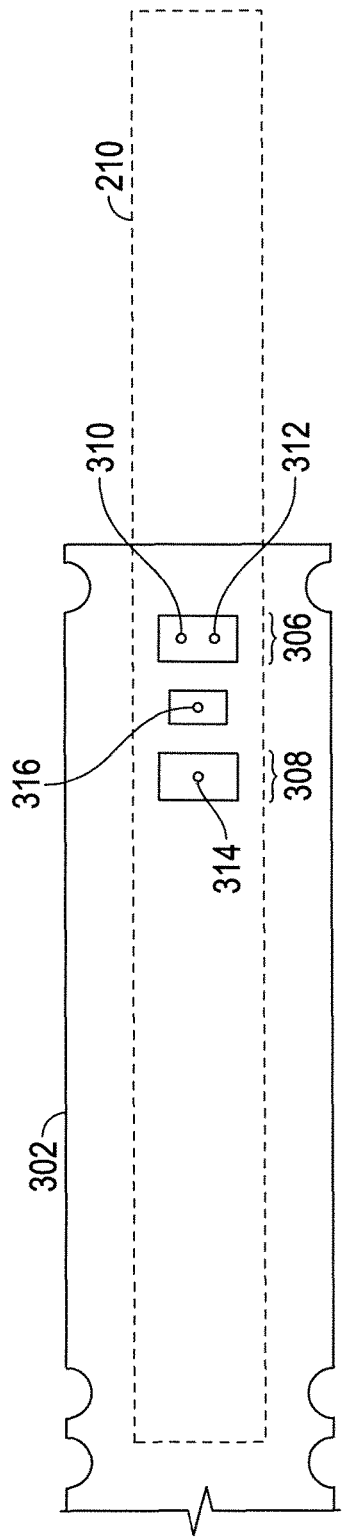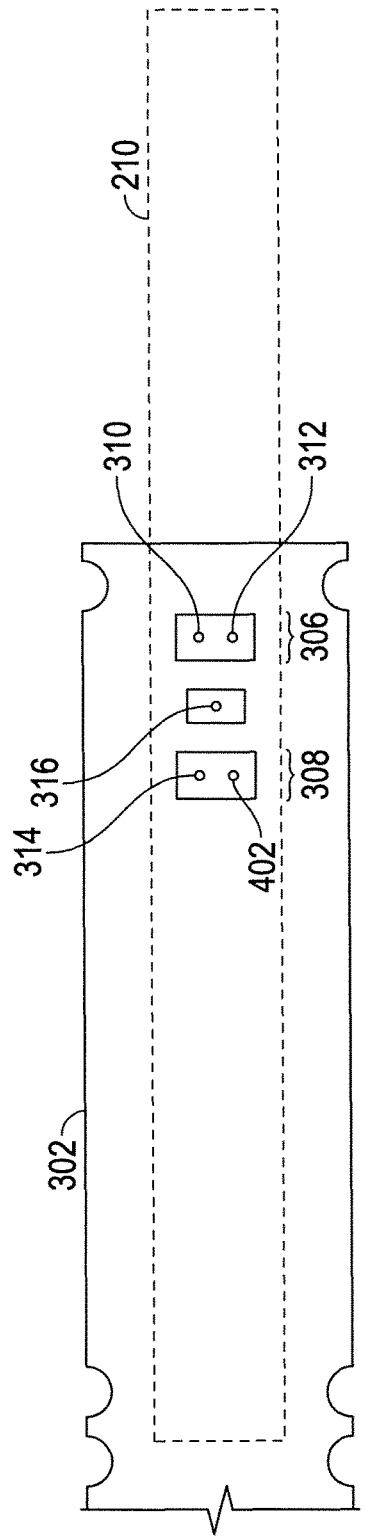

DEVICES AND METHODS FOR ELECTRONIC ANALYTE ASSAYING

BACKGROUND OF THE INVENTION

Field of the Invention

The present invention relates generally to diagnostic assays for analytes in a fluid sample. In particular, the invention relates to devices and methods for detecting an analyte in a bodily fluid.

Description of the Related Art

Detection of human chorionic gonadotropin (hCG) in urine samples is routinely used to determine a woman's pregnant/non-pregnant status. Traditional one-step pregnancy test devices detect hCG by utilizing a double antibody system in a lateral flow format resulting in a "sandwich" complex of hCG, a capture antibody and a labeled antibody, which is captured at a specific detection area on a test strip. A digital version of the pregnancy test device consists of an opto-electronic reader powered by an internal battery that measures the absorbance/reflectance of the label particles specifically captured at the detection area of the test strip and automatically subtracts any non-specific background color from an adjacent area of the test strip that is outside the detection area. The adjusted measurement of absorbance/reflectance of accumulated label particles at the detection area is processed to generate a detection determination for display as a clearly read YES+/PREGNANT or NO−/NOT PREGNANT digital result on a liquid crystal display (LCD) screen.

Although electronic readers provide the added convenience of eliminating the end-user step of interpreting the results of the test, a step required in traditional lateral flow devices, there is room for improvements.

SUMMARY OF THE INVENTION

The devices and methods described each have several aspects, no single one of which is solely responsible for its desirable attributes. Without limiting the scope of this disclosure as expressed by the claims which follow, some features will now be discussed briefly. After considering this discussion, and particularly after reading the section entitled "Detailed Description," one will understand how the features described provide advantages that include more accurate and consistent detection of an analyte through the use of multiple sensor inputs.

In one innovative aspect, a disposable analyte detection device is described. The device includes a receiving member configured to receive a test strip including a test region and a background region laterally displaced along the length of the test strip. The device further includes a first plurality of sensors placed such that the first plurality of sensors are located above the test region once the test strip is received. The device also includes at least one background sensor placed such that the background sensor is located above the background region once the test strip is received. The device further includes a light source placed such that the light source illuminates the test region and the background region once the test strip is received.

The device also includes a processor. The processor is configured to receive test region signals indicating a quantity of light reflected from the test region. The test region signals are received from each of the first plurality of sensors. The processor is configured to receive background signals indicating a quantity of light reflected from the background region. The background signals are received from the background sensor. The processor is also configured to generate a detection result based on the received test region signals and the received background signals.

In another innovative aspect, a method of detecting an analyte is described. The method includes receiving test region signals indicating a quantity of light reflected from a test region included on a test strip from each of a first plurality of sensors. The method includes receiving background signals indicating a quantity of light reflected from a background region included on the test strip from a background sensor. The method further includes generating a detection result based on the received test region signals and the received background signals.

In a yet another innovative aspect, a disposable analyte detection device is described. The device includes means for receiving test region signals indicating a quantity of light reflected from a test region included on a test strip from each of a first plurality of sensors. The device includes means for receiving background signals indicating a quantity of light reflected from a background region included on said test strip from a background sensor. The device also includes means for generating a detection result based on said received test region signals and said received background signals.

Details of one or more implementations of the subject matter described in this specification are set forth in the accompanying drawings and the description below. Other features, aspects, and advantages will become apparent from the description, drawings, and claims. Note that the relative dimensions of the following figures may not be drawn to scale.

BRIEF DESCRIPTION OF THE DRAWINGS

FIGS. 1A and 1B show perspective views of a digital detection device.

FIGS. 2A and 2B show perspective views of another digital detection device with a removable test stick.

FIG. 3 shows a functional block diagram of an embodiment of a printed circuit board for an exemplary digital analyte detection device.

FIG. 4 shows a functional block diagram of another embodiment of a printed circuit board for an exemplary analyte detection device.

DETAILED DESCRIPTION OF THE INVENTION

Figure 5:
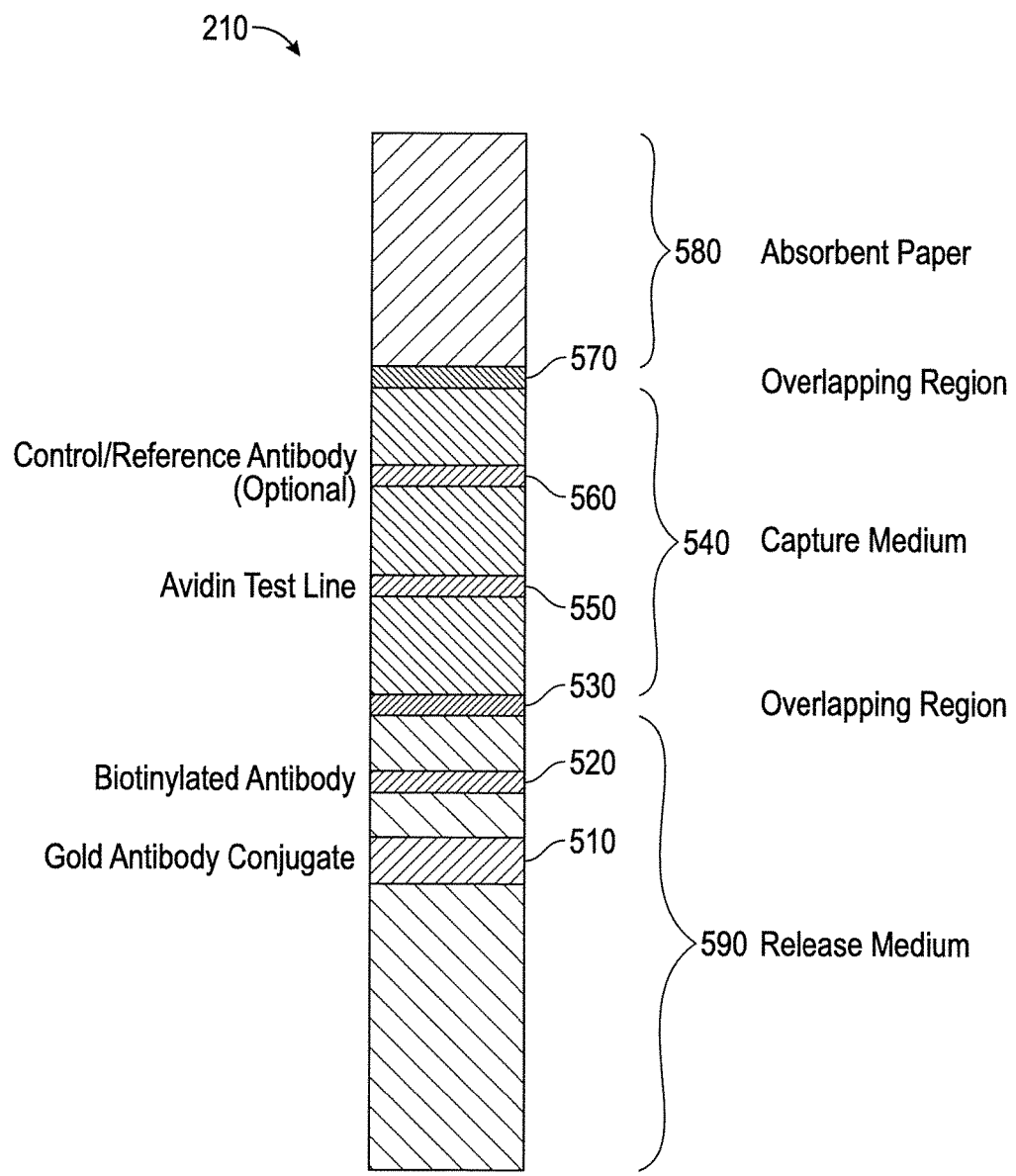
FIG. 5 is a diagram of an example of a triphasic test strip suitable for use in an implementation of the invention.

For an electronic reader system that incorporates a lateral flow test strip, one of the many challenges in increasing the detection sensitivity is the unpredictability of uneven migration of resolubilized reagents and sample flow which can affect the electronic interpretation of the test result resulting in an inaccurate or inconsistent test result determination. Unlike the lateral flow pregnancy test where the consumer merely looks for the presence of a line irrespective of its color intensity and its uniformity, in a digital pregnancy test it is extremely important that the test line is uniform in color intensity. However, this is not always possible due to the reasons cited above. Therefore, improved devices, methods, and test kits for electronic analyte assaying digital detection are desirable.

Described herein are devices and methods for improving the detection of analytes. Specifically, the provided features can provide a non-limiting advantage of accurate detection in the presence of channeling. Channeling generally refers to the situation where a fluid sample applied to a test strip unevenly travels along the test strip toward the test region. This can result in an uneven reaction at the test region thereby affecting the detection.

One way channeling can affect the result is by causing uneven or inconsistent test line development. The detection of color inconsistencies within the line development by the additional sensor placement, as described in further detail below, provides an option to obtain more information regarding test line development across the line rather than is available from a single sensor measurement position.

Another variance caused by channeling is an uneven background. Some configurations as described herein have the ability to detect broader background areas. Thus, the problem of uneven streaks or background residues that can lead to a false interpretation of test results can be minimized.

Another factor which may affect the result is the quality of the test strip. In some instances, variations in the manufacturing of a test strip may result in dashed, broken, or uneven test line development. Examples of the variations are the application of reagents on the test strip or in the reagents applied.

Inconsistencies in the assembly or component molding process can also result in uneven compression points along the test strip. This uneven compression is a further factor which can affect the result because the pressure may create an uneven migration flow of the sample and/or the resolubilized reagents. The result of the uneven migration can be a non-uniform color across the test line.

The capture medium is another factor affecting test accuracy. Variations in the porosity of the capture medium can result in uneven streaks which can lead to an incomplete and/or uneven test line development. For example, nitrocellulose has an inherent porosity variation of up to 50%.

A further factor which can affect the result is the volume of sample applied. For example, in an assay utilizing urine, variations in the volume of sample applied onto the urine wick can affect the efficiency of conjugate resolubilization. The consistency of conjugate resolubilization, migration, and/or test line development is dependent in part on the volume applied. Low or excessive volume can adversely impact the test result.

To help alleviate these factors, an improved detector and method was developed. Additional optical sensors are included to enhance detection. The sensors are placed within proximity of the detection area(s) on the test strip to increase sensor coverage of the test line and background test areas.

One detection layout features the placement of a light emitting diode (LED) between the front (e.g., reaction) sensor and rear (e.g., sample or background) sensor. One implementation features two front sensors with two background sensors. Another implementation includes two front sensors with one background sensor.

The LED is configured to shine light on one or more regions of the test strip. The sensors are configured to receive light reflected from the illuminated regions. Based on the quantity of light detected, an analyte detection determination can be generated.

For example, in the implementation featuring two front sensors and two background sensors, a generated detection value can be based on one or more of: readings of left front sensor and left background sensor; readings of left front sensor and right background sensor; readings of right front sensor and left background sensor; and/or readings of right front sensor and right background sensor.

In an implementation including two front sensors with one background sensor, a generated detection value can be based on one or more of: readings of left front sensor and background sensor; and/or readings of right front sensor and background sensor.

The integration of the additional sensors enables the placement of more detection zones within a specified region of the detection area (e.g., test line). For example, the additional detection zones create specific sensor coverage in the left side and right side of the test strip. This configuration can provide additional coverage of most if not the entire region of interest (e.g., test line). The methods described utilize reflectance values from the sensors. By increasing the sensor coverage, detection of various types of background unevenness may be detected including migration streaks.

The background may include streak formations due to the variation factors discussed above. In configurations where a single sensor is located above a region of interest, depending on the type of streak(s), the single sensor may not identify the streak(s). This may result in a false test result. To provide an accurate result, both the test and the background sensors may be configured to provide information for streak detection.

Accordingly, having the values from two sets of sensors may provide signals for the detection method to select and determine the presence or absence of the test line. In the event there is uneven migration and/or test line development, dark and light intensity areas may be identified within the detection area. With the availability of values from zones, the methods described process test values to derive a sensitive and/or specific test result.

For example, the test result may be generated based on an average of the four zones or a combination of a sub-set of zones. The test result may be generated based on the highest values detected.

More sophisticated detection methods may include a "majority rules" approach. In such an implementation, values that have been calculated from all the zones may be initially considered. Depending on the number of zones needed to meet the set threshold, a determination is made based on the majority of zones fulfilling the previously established criteria.

Another detection method may include value difference between zones. For example, differences in values between left and right zones can be used as a "check" for validity (e.g., streaky test) and/or detection determination.

Depending on the assay being performed, the device may be dynamically configured to provide the optimal checks and detection method. For example, in a two-two configuration, sixteen possible calculation combinations may exist. For a given assay, certain variations may be more prevalent. For example, a certain reagent may be more prone to streaking or the sample fluid may be more likely to experience low volume. In such an assay, the device may be configured to utilize more combinations than an assay which is less prone to streaking. This can allow a single device to be manufactured which can accurately perform a variety of assays.

Various aspects of the novel apparatuses, test kits, and methods are described more fully hereinafter with reference to the accompanying drawings. The teachings disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel apparatuses, test kits, and methods disclosed herein, whether implemented independently of or combined with any other aspect of the invention. For example, an apparatus may be implemented or a method may be practiced using any number of the aspects set forth herein. In addition, the scope of the invention is intended to cover such an apparatus or method which is practiced using other structure, functionality, or structure and functionality in addition to or other than the various aspects of the invention set forth herein. It should be understood that any aspect disclosed herein may be embodied by one or more elements of a claim.

Although particular aspects are described herein, many variations and permutations of these aspects fall within the scope of the disclosure. Although some benefits and advantages of the preferred aspects are mentioned, the scope of the disclosure is not intended to be limited to particular benefits, uses, or objectives. Rather, aspects of the disclosure are intended to be broadly applicable to different detection technologies and device configurations some of which are illustrated by way of example in the figures and in the following description of the preferred aspects. The detailed description and drawings are merely illustrative of the disclosure rather than limiting, the scope of the disclosure being defined by the appended claims and equivalents thereof.

An improved diagnostic test that determines a woman's pregnant/non-pregnant status by detecting clinically significant and very low levels (e.g., 3-5 mIU/mL) of human chorionic gonadotropin (hCG) in urine is used in the following description to illustrate various innovative aspects. The test comprises a test strip containing reagents for the detection of hCG and an electronic reader that measures color development at a detection area of the test strip and converts it to an electronic or digital signal. Although the detection of hCG in urine is used to describe the invention, this disclosure is applicable to the qualitative or semi-quantitative detection of low levels of any analyte in a biological sample.

FIGS. 1A and 1B show perspective views of an exemplary digital detection device. The digital detection device 10 includes a cap 14. FIG. 1A illustrates a perspective view of the device 10 with the cap 14 intact, while FIG. 1B illustrates a perspective view of the device 10 with the cap 14 removed. The device also comprises an outer, molded casing 12 which defines a hollow, elongate enclosure. Casing 12 is configured to provide a recessed portion 20 shaped to permit users to place their thumb into the recessed portion and their forefinger on the bottom of the casing 12 to securely hold the device 10. A central section on the top of the casing 12 defines a centrally located window 40 which permits a user to observe test results. Inside the casing 12 is a lateral flow test strip and electronic components, details of which will be described further below. Casing 12 defines a sample receiving member 16 onto which a fluid sample can be applied to the test strip in the device 10. A removable cap 14 can be secured to one end of the casing enclosure over the sample receiving member 16. Sample receiving member 16 is positioned so that part of the sample receiving member is received in the casing enclosure and part of the sample receiving member 16 extends from the end of the casing enclosure. In this embodiment, color or reflectivity changes are sensed electronically, and the results are presented to a user on a display 42. The display 42 may render various icons or messages to a user, such as test results, device status, or error messages. The display 42 may be color or monochrome. In one embodiment, the display 42 is a liquid crystal display (LCD).

FIG. 2A shows another perspective view of an exemplary digital detection device without an integral test strip. In this embodiment, as described in more detail with reference to FIG. 2B, the test strip may be part of an insertable and removable test stick. A device 100 may be formed from plastic, metal, or other material. The device 100 includes a test stick acceptor port 110. The test stick acceptor port is designed to receive test sticks including test strips for analysis. The device 100 also includes a display 120. The display 120 may render various icons or messages to a user such as test results, device status, or error messages. The display 120 may be color or monochrome. In an example implementation, the display 120 may be a liquid crystal display (LCD). The device 100 may further include a test stick alignment marker 130. In the example shown, the test stick alignment marker 130 is a triangle pointing to the test stick acceptor 110. The test stick alignment marker aids with insertion of a test stick into the device 100. The device 100 may include a test stick ejector 140. The test stick ejector 140 may be a manual or electronic mechanism to eject a previously inserted test stick from the device 100.

FIG. 2B shows another perspective view of an exemplary digital detection device with a disposable test stick inserted therein. In the example shown, the device 100 is accepting a test stick assembly 200 housing the actual test strip 210. It is desirable for the test stick assembly 200 to couple with the device 100 so that the test stick assembly 200 will not fall out of the device 100 and may form a water resistant seal to protect a portion of the device 100 from fluid samples collected via the test stick assembly 200. The coupling should also minimize ambient light leakage into the device when testing is being performed on a test strip. Fluid samples collected via the test stick assembly 200 are generally urine, although depending on the test being performed, could be blood, sweat, tears, saliva, or any bodily fluid. An example test strip 210 will be described below in reference to FIG. 5. The test stick assembly includes a test stick housing 220. In an implementation, the test stick housing 220 may be formed from plastic. The test stick assembly 200 includes a test stick alignment marker 230 corresponding with the test stick alignment marker 130 on the device 100. The test stick assembly 200 may also include a clicking sound feature to indicate proper alignment and insertion into device 100.

FIG. 3 shows a functional block diagram of an embodiment of a printed circuit board for an exemplary digital analyte detection device. The printed circuit board 302 may be housed, for example, in the digital detection devices of FIGS. 1A, 1B, 2A, and 2B. The printed circuit board 302 has sensors 310, 312, and 314 as well as an emitter such as a light source 316 mounted thereon. The housing includes these components such that the sensors and the light source are in position to interact (e.g., transmit/receive light to/from) with test strip 210. Printed circuit board 302 can be in any shape or size that allows the sensors 310, 312, and 314 and the light source 316 to be placed in an appropriate place to interact with the test strip 210, which is shown in dotted outline positioned over the printed circuit board and the components mounted thereon. In some embodiments, the printed circuit board 302 is fixed inside a hand-held housing such as shown in FIGS. 1A, 1B, 2A, and 2B, and the test strip 210 is appropriately positioned adjacent to the printed circuit board 302 so that the desired area of the test strip is illuminated by the light source 316 and reflected light intensity can be measured by the sensors 310, 312, and 314. The test strip 210 can be inserted, during or after device manufacture, into the housing, such that the sensors 310, 312, and 314 and the light source 316 are positioned over the test strip. The housing can also house additional components beyond sensors 310, 312, and 314 and light source 316, such as various information displays, circuitry, antenna, power source, and the like.

Test strip 210 can be made of any suitable material, a wide variety of which are known in the art. In some embodiments, test strip 210 may be formed from an absorbent material to aid in fluid collection. The purpose of test strip 210 is to collect fluid samples with which to perform analyte detection. Fluid samples collected via test strip 210 are generally urine, although depending on the test being performed, could be blood, sweat, tears, saliva, or other fluid samples.

Test strip 210 can divided into test region 306 and background region 308. In some embodiments, test strip 210 may be divided into additional regions. The various regions of test strip 210 may have different characteristics, including being made of different materials or being designed to have different fluid absorption and transport characteristics.

As explained above, light source 316 is mounted on the printed circuit board 302. Light source 316 is designed to shine light onto test strip 210. Light source 316 can be any type of light source. In some embodiments, light source 316 can be a light emitting diode (LED) or other similar small, low power light source.

As explained above, sensors 310, 312, and 314 may also be mounted on printed circuit board 302. Sensors 310, 312, and 314, are designed to detect light produced by the light source 316 and reflected off of the test strip 210. Sensors 310, 312, and 314 can be positioned such that they detect reflected light from different areas of test strip 210. FIG. 3 shows an implementation where the sensors 310 and 312 are positioned to detect light reflected from two areas or zones in test region 306 and sensor 314 is positioned to detect light reflected from an area or zone of background region 308. The light detected by the sensors can be used to calculate reflectance values for each zone of the test strip. These reflectance values can be used to determine a result of the analyte detection. The result can be calculated based on the average of the reflectance values of the various zones, the highest or lowest value among the zones, whether certain number of zones meet a threshold requirement, the differences between the reflectance values among the zones, and the median of the reflectance values among the zones. Additional methods of determining the result can be used. The specific operation of different implementations of the sensors and detection is described further below.

The use of multiple sensors above an area on the test strip can help mitigate the variations discussed above. In one implementation, the multiple sensors are evenly distributed above the test area with the centers of each sensor aligned. In some implementations, it may be desirable to place the sensors above the test area with a slight offset between the center points of the sensors. The offset may be based on the longitudinal extent of the area of interest. For example, if the test area measures 2 mm along the strip, the two sensors may be placed with a 0.5 mm center offset. This can help account for variations between the front and back of the test area in addition to the sides. In some implementations, the sensors may be placed relative to mounting points which are adjacent to the test strip. Such an implementation may provide enhanced detection by accounting for uneven compression points along the test strip. For example, a pair of sensors may be placed such that they detect respective regions to the right and left of a compression point.

Similar placement principles can be applied for a three sensor configuration. The sensors may be evenly distributed above the area of interest. The sensors may be offset, forming a "W" shape.

In implementations including two areas of interest (e.g., test site and background area), one area may include multiple sensors while the other may include only one sensor. For example, two sensors may be used for the test site and one sensor for the background area. The single background sensor may be placed such that it can detect the background at the center of the test strip. In such a configuration, the three sensors may form a triangle.

In some implementations, two sensors may be used for the test site and two sensors may be used for the background. In such an implementation, the center of the leftmost test site sensor may be aligned with the center of the leftmost background sensor. Similarly, the center of the rightmost test site sensor may be aligned with the center of the rightmost sensor. In some implementations, it may be desirable to offset the sensors.

Table 1 below illustrates various combinations of sensors and the pattern formed by the sensors which may be included in embodiments of the printed circuit board.

TABLE 1

| Number of Test Area Sensors | Number of Background Sensors | Sensor Layout Pattern |
|---|---|---|
| 2 | 1 | Triangle |
| 2 | 2 | Square |
| 2 | 2 | Parallelogram |
| 3 | 1 | Triangle |
| 3 | 1 | Arrowhead |
| 3 | 1 | Diamond |
| 3 | 2 | Rhombus |
| 3 | 3 | Square |
| 3 | 3 | Bow-tie |
| 3 | 3 | Hexagon |
| 3 | 3 | Arrow tail |
| 2 | 3 | Rhombus |

FIG. 4 shows a functional block diagram of another embodiment of a printed circuit board for an exemplary analyte detection device. The printed circuit board 302 may be housed, for example, in the digital detection devices of FIGS. 1A, 1B, 2A, and 2B. The implementation shown in FIG. 4 is similar to the printed circuit board shown in FIG. 3. However, in FIG. 4, an additional sensor 402 is added to provide multiple sensors placed to detect both regions of the test strip.

FIG. 5 is a diagram of an example of a triphasic test strip suitable for use in an implementation of the invention. However, it will be appreciated that a wide variety of test strip designs may be used. The test strip 210 shown in FIG. 5 may be included in device 10 shown in FIGS. 1A and 1B or included in the test stick assembly 200 shown in FIG. 2B. The fluid path along the test strip 210 will be discussed starting with the bottom of the figure and moving up. It will be recognized that this spatial orientation is merely a convenience. At the bottom of the test strip 210, a fluid sample may be applied. The test strip 210 may be formed from an absorbent material to aid in the uptake of the fluid sample.

The fluid sample may encounter a conjugate region 510. In the example shown, the conjugate region 510 is a colloidal gold antibody conjugate region where the applied fluid sample will solubilize the gold antibodies, so that gold labeled antibodies will bind to the analyte of interest (e.g., hCG) when the analyte is present in the sample. As the fluid sample passes through the conjugate region 510, analyte in the fluid sample will bind the gold conjugated antibody in the liquid phase and carry the conjugate-analyte complex along the test strip. The fluid sample may then pass through a second antibody region 520. In the example shown, the second antibody region 520 includes biotinylated antibody (antibody chemically coupled to biotin) that specifically binds to a different epitope on the analyte of interest than the gold conjugated antibody, forming a "sandwich" complex of analyte and two antibodies, one with colloidal gold, and the other with biotin. The sandwich complex may then be carried further along the test strip across a first overlapping region 530. The area from the start of the test strip 210 to the first overlapping region 530 may generally be referred to as the release medium 590.

After the overlapping region 530, the test strip 210 includes a capture medium 540. As the fluid sample continues along the test strip 210, the sample next encounters a test region 550. In the example shown in FIG. 5, the test region 550 includes an avidin test line for binding the biotin on the second antibody to capture the sandwich complex (with the gold) at the test line. The test region or a portion thereof 550 will thus become darker as more of the sandwich complexes are accumulated. In an example implementation where the conjugate comprises colloidal gold, the electronics system, which may include sensors and/or a processor for performing a transformative algorithm on sensed data, may measure the colloidal gold specifically bound at the test region 550 of the test strip 210. After the test region 550, the test strip 210 may include a region downstream from the test line 550 which may be referred to as downstream region 560. In some embodiments, this downstream region 560 may include fixed antibodies or other proteins that bind to the gold conjugated antibody. This can be used to detect gold bound antibody in the fluid that is not specifically bound to the analyte so that gold labeled antibody solubilization and migration up the test strip and through the test region 550 can be confirmed even when no analyte is present in the applied sample. In other embodiments, downstream region 560 includes no antibodies and is simply a defined region of the capture medium 540, which may be referred to as a background region. In these embodiments, this region can be used to measure reflectance changed due to wetness and residual gold labelled antibody in the strip that interfere with accurate test region 550 measurements. Test strips with no antibody in the downstream region 560 may be advantageous because it eliminates the need for the antibodies at this region, reducing cost of the test strip. When used as a background region, it may not be necessary for this region 560 be downstream of the test line 550. Reflectance measurements from the test line 550 and/or downstream region 560 may be used separately to define successful testing and analyte concentrations.

The capture medium 540 may terminate with a second overlapping region 570. The second overlapping region 570 may serve as a border between the capture medium 540 and an absorbent portion 580 of the test strip 210. The absorbent portion 580 of the test strip 210 facilitates the uptake of the fluid sample as it arrives at the end of the test strip 210.

Test strips of this nature are known in the art, and are described in more detail in, for example, FIGS. 2-6 and the accompanying description of U.S. Pat. No. 6,319,676, the entire content of which is hereby incorporated by reference.

It may be desirable to align the test strip 210 when inserted into a digital detection device, such as the digital detection device 10 shown in FIG. 1 or the digital detection device 100 shown in FIG. 2, such that the capture medium region is substantially located under sensors such as sensor 310 and/or sensor 312. Two or more sensors (e.g., sensor 310 and/or sensor 312) may be located directly over the test region 550. At least one second sensor (such as sensor 314 and/or sensor 402) may be located directly over a second region 560 of the test strip that may or may not contain a control/reference line. A light source (e.g. light source 316) may be positioned with respect to the regions 550 and 560 to simultaneously illuminate both. Measurements of the reflectivities of regions 550 and 560 provide a measure of analyte concentration.

Figure 6:
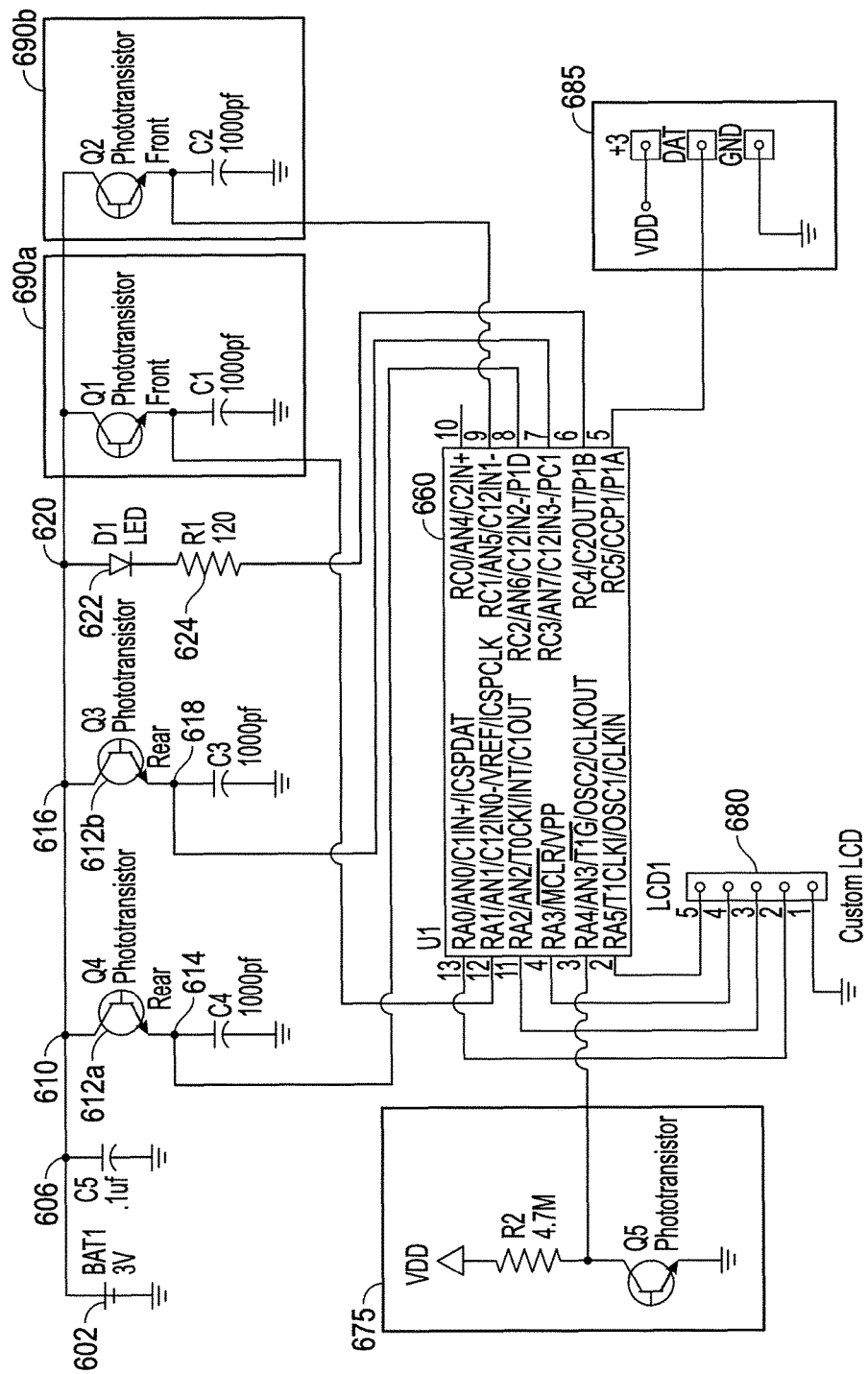
FIG. 6 is a circuit diagram of an example circuit suitable for use in a digital detection device.

FIG. 6 is a circuit diagram of an example circuit suitable for use in a digital detection device. For example, the devices shown in FIGS. 1-4 may include one or more elements shown in FIG. 6. The circuit diagram illustrates a configuration including two sensors which may be positioned over a first area of the test strip and two sensors which may be positioned over a second area of the test strip. The shown configuration generally corresponds with the circuit board shown in FIG. 4. The circuit diagram shown includes various voltage, capacitance, resistance, and similar values for several elements shown. It will be understood these values are simply examples and other (e.g., different) voltages, capacitance, and/or resistance values may be used.

The circuit shown includes a battery 602. One terminal of the battery 602 is coupled to ground. The other terminal of the battery 602 is coupled to a node 606. A first branch from the node 606 is coupled to a capacitor 608 which is then coupled to ground. The second branch from node 606 is coupled to a node 610.

The node 610 provides a first branch to a sensor 612a. As shown in FIG. 6, the sensor 612a is a phototransistor. The sensor 612a shown in FIG. 6 may be the rear left sensor configured to detect reflectance from the background area. In light based sensing configurations, when activated by light, the sensor 612a applies a voltage to a node 614. The node 614 includes two branches, one to a capacitor which is connected to ground and one branch to a processor 660. The processor 660 shown in FIG. 6 is a PIC16F616 by Microchip Technology Inc. which is one example of a commercially available processor which may be included in the circuit. The processor 660 is configured to obtain and process the voltage from the phototransistor 612a. The voltage can be used as an indication of the quantity of analyte contained on the sensed area.

The node 610 includes a second branch to a node 616. The node 616 provides a first branch to a sensor 612b. The sensor 612b shown in FIG. 6 is a phototransistor. The sensor 612b shown in FIG. 6 may be the rear right sensor configured to detect reflectance from the background area. In light based sensing configurations, when activated by light, the sensor 612b applies a voltage to a node 618. The node 618 includes two branches, one to ground and one to the processor 660. The processor 660 is further configured to obtain and process the voltage from the sensor 612b. The voltage can be used as an indication of the quantity of analyte contained on the sensed area.

The node 616 includes a second branch to a node 620. The node 620 includes a first branch to a light source 622. As shown in FIG. 6, the light source 622 is an LED. Coupled to the light source 622 is a resistor 624. The resistor 624 is then coupled with the processor 660. The processor 660 may control the illumination of the light source 622 as described herein.

The second branch of the node 620 is coupled to a sensor assembly 690a. Another sensor assembly 690b is also included in the circuit. The sensor assemblies 690a and 690b shown are front sensor assemblies. The assemblies 690a and 690b are substantially similar to the elements coupled to nodes 610 and 616. Each assembly provides a further voltage to the processor 660 indicating the reflected light from the test strip for the corresponding assembly.

It should be noted that the sensors 612 and the light source 622 are coupled in parallel. This allows simultaneous operation of the emission and detection for all monitored areas. Such coordination can help increase the accuracy of validity determination and test result determination because discrepancies due to sample timing can be reduced and/or eliminated. The parallel readings also provide a common point of reference for all sensed values.

Also shown in FIG. 6 is a data logging module 685. The data logging module 685 is coupled to the processor 660 and is configured to store information for the device. For example, the data logging module 685 may store diagnostic information regarding the state of the device (e.g., power level, time of operation, number of readings obtained, and the like). The data logging module 685 may provide or be coupled to an export interface such as a USB interface (not shown).

Also shown in FIG. 6 is a display 680. The display 680 shown is an LCD display though the display 680 may be an LED display, or other component configured to provide indications. In some implementations the indication may be audible. In such implementations, the display 680 may be replaced with or used in conjunction with a speaker (not shown).

FIG. 6 also includes a wake-up detector 675. The wake-up detector 675 includes a sensor configured to determine whether the device should exit a sleep state and prepare for test. As shown in FIG. 6, the wake-up detector 675 includes a phototransistor. In such an implementation, when the device is removed from the packaging, light received by the wake-up detector 675 can be used to initiate the testing. The wake-up detector 675 is configured to provide a voltage to the processor 660 upon detecting the wake-up condition. Other examples of wake up conditions include temperature, humidity, pressure (e.g., barometric), motion, or the like.

Assay hardware such as that illustrated in FIG. 6 can be programmed and operated to perform assays in a variety of ways. Typically, there is some test protocol initiation event that the device recognizes. This can be done with the wake up detector described above with reference to FIG. 6, a conductivity sensor that senses a fluid sample application to the assay strip, or a button the user pushes. After test initiation, light emission(s) and corresponding reflectivity measurements occur. In some cases, a device may simply wait a pre-determined time after test initiation, and then at the end of the pre-determined time, take one reflectivity measurement of the test region and the background region of the test strip. An assay result may be then be computed from a single measurement. In other implementations, a series of measurements over the course of reagent development may be taken, and an assay result may be computed from one or more measurements taken after a pre-determined time has elapsed or after reagent development has stabilized.

Figure 7:
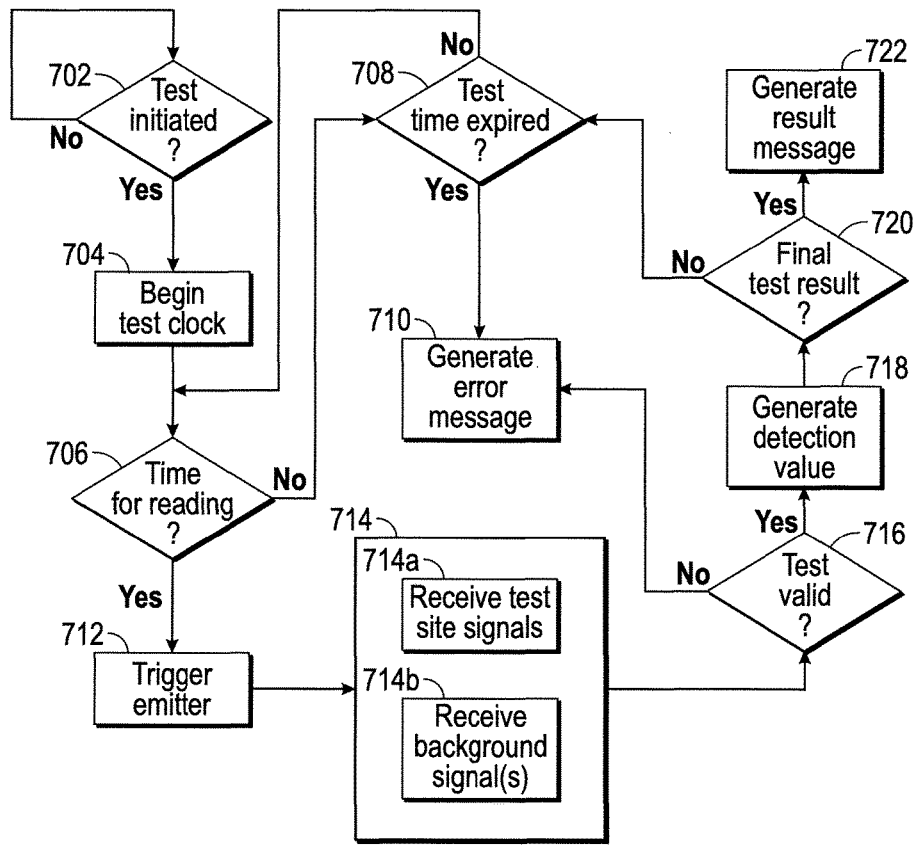
FIG. 7 is a flow diagram of an exemplary process for detecting a monitored analyte.

FIG. 7 is a flow diagram of an exemplary process for detecting a monitored analyte. The process shown in FIG. 7 may be implemented in whole or in part by one or more of the devices described above such as shown in FIGS. 1-4 or FIG. 6.

The process begins by determining whether the test has been initiated at determination node 702. As the device may be a disposable device, it may be desirable in some implementations to maintain a low power state while the device is not in use. One way to achieve this is to include an additional sensor to detect when the device is removed from its packaging. For example, a light sensor may be included on the printed circuit board which receives light through the housing. When manufactured, the device may be placed in an opaque packaging which prevents light from being transmitted to the light sensor. One example implementation is the wake-up detector 675 shown in FIG. 6. Once the device is removed from the packaging, light may be transmitted through the housing to the light detector. This detection may signal the initiation of a test.

In some implementations, the initiation of a test may be indicated by insertion of a test strip into the receiving member. In some implementations, the initiation of a test may be indicated by detecting application of a fluid sample to the test strip. For example, a circuit may be completed once the fluid sample is applied. This completion may indicate the initiation of the test.

If the test has not been initiated, the process remains at determination node 702. If the test has been initiated, at node 704 a test clock may be started. The test clock may be included to define the duration of the test. The test clock may further define a known reflectance data sample rate to control the detection process. The test clock may be a relative clock (e.g., relative to the initiation detection). In some implementations, the test clock may be an absolute clock (e.g., configured to provide time and date information). In some implementations, the start time may be stored in a memory for further processing. The test clock may be included in a microcontroller and coupled to one or more of elements included in the detection device.

At decision node 706, it is determined whether the time to take a reading has arrived. The time to take a reading may be defined in a variety of ways. In some implementations, one or a series of reading times may be specified in a memory included in the device. In some implementations, the time to take a reading may be based on some form of control measurement indicating that the test has reached a particular state of development or that no testing errors have been detected. If the time to take a reading has not arrived, the process continues to decision node 708.

At decision node 708 a determination is made at the expiration of the test time. It may be desirable to declare a test over if a reading has not been received after a certain period of time. This is especially the case when a separate control determination is made to define when and/or whether to take a test reading. This can ensure the device is in a proper state to generate a detection result before a reading is actually taken. The determination may be based on a comparison of the time indicated by the test clock and a predetermined duration. In implementations including a relative clock, the duration may identify a number of cycles to allow the test to run. If the clock exceeds the duration, the test time may be expired. In implementations including an absolute clock, the determination may be based on the stored start time, current clock time and duration. If the elapsed time as determined by comparing the start time with the current time exceeds the duration, the test time may have expired.

If the time has expired without a reading having been taken, at node 710, an error message is generated. The error message may be an error code. The error code may be used by the device to select and display an indication of the error. For example, an error icon may be displayed on an LCD display included in the device upon receipt of the error message. This provides a meaningful indication to the user of the test status.

Returning to decision node 708, if the test time has not expired, the process returns to decision node 706 to determine whether the time has arrived for taking a reading. If the time has arrived, at node 712, an emitter is triggered. The emitter may be a light emitter such as an LED. Another example of an emitter is an electronic pulse emitter. Triggering the emitter causes the emitter to transmit an emission toward the test strip. Specifically, the emitter transmits an emission toward the test area and the background portions of the test strip. In some implementations, multiple emitters may be included and simultaneously triggered.

At node 714, signals are received. As shown in FIGS. 3, 4, and 6, for example, multiple sensors may be arranged over the test site. Accordingly, at node 714a, multiple test site signals are received. The received signals indicate a quantity of an emission transmitted from the test site. For example, in an implementation including a light source as the emitter, the test site signals may be received by two or more photodetectors. The test site signals in this implementation indicate a quantity of light reflected from the test site.

At node 714b, one or more background signals are also received. In one implementation, a single background sensor is used. This sensor is placed over the background area on the test strip and receives reflected illumination from the background area. For example, in an implementation including a light source as the emitter, the background signal may be received by a photodetector. The background signal identifies a quantity of light reflected from the background area. This information can be used as part of the analyte detection process as described further below.

In some implementations, the received signals are stored in a memory of the device. The received signals are stored such that the sensor generating the signal can be identified. For example, an information field may be associated with the signal identifying the sensor. In some implementations, separate memory or memory partitions may be used to store the readings for corresponding sensors. While this configuration may simplify the data stored, it may increase the memory management included in the device. The received signals may also be stored with a time reading indicating when the signal was received. In some implementations, the readings may be stored sequentially without reference to time.

The received signals may be used at decision node 716 to determine whether the test is valid. The validity of the test may be determined based on the received signals. The signals used may be the currently obtained signals. For example, one or more of the background signals may be compared to a threshold and, if the signal value exceeds the threshold, the test declared invalid. The threshold may be stored in a memory of the detection device.

In some implementations where multiple sensors are included for an area, all or a portion of the signals sensed for the area may be compared to each other. In one implementation, if the difference between the measurements from two test line sensors or two background sensors exceed a threshold the test may be declared invalid. Validity may be further determined based on a comparison of the currently received signals and previously received signals. For example, trends may be used to identify valid tests. One example of trend detection is described in U.S. patent application Ser. No. 13/402,024 which is commonly owned and assigned and is hereby expressly incorporated by reference in its entirety.

Validity may be determined based on a combination of the above discussed factors. For example, validity may be a multifactor determination based on intra-sensor area readings (e.g., for all sensors over an area) and inter-sensor area readings (e.g., comparison of one sensor for a first area with a second sensor for a second area).

In some implementations, it may be desirable to store one or more values generated as part of the validity determination for further processing. For example, the average value for a sensor area may be used in generating an analyte detection value as will be described below.

If the test is determined to be invalid, at node 710, an error message is generated as described above. If the test is determined to be valid, at node 718, a detection value is generated. For example, in the implementation featuring two front sensors and two background sensors, a generated detection value can be based on one or more of: readings of left front sensor and left background sensor; readings of left front sensor and right background sensor; readings of right front sensor and left background sensor; and/or readings of right front sensor and right background sensor.

In an implementation including two front sensors with one background sensor, a generated detection value can be based on one or more of: readings of left front sensor and background sensor; and/or readings of right front sensor and background sensor.

The generated detection value may compare the sensed values to one or more thresholds to determine whether the fluid sample includes the analyte of interest. For example, a test region signal from one of multiple sensors configured to detect light reflected from the test area may be combined with a background signal. If the sensed values or combination thereof exceed the threshold, the detection value may positively identify the presence of the analyte.

The generated detection value may be stored in a memory. The generated value may be associated with a time at which the value was generated. In some implementations, generated values may be stored sequentially indicating the development of the test over time.

At decision node 720, a determination is made as to whether the final test result is obtained. As discussed above, a single reading may not be sufficient to accurately generate a final test result. Accordingly, the generated result value may be compared to a final result threshold value. If the generated value is less than the threshold the confidence level in the accuracy of the result may be in question. Accordingly, the process may continue to decision node 708 as described above.

If the determination at node 720 indicates the test result is sufficient, at node 722, a result message is generated. The result message may be a result code which can be used by the display of the device to render a clear indication of the test result.

As noted above, a variety of processing algorithms may be applied to the multiple sensor outputs to determine test result output at node 722. In some advantageous implementations, the output is a binary result such as YES or NO. In these implementations, particular processing algorithms may be especially useful. It is possible, for example, to compute the average reading for the test line sensors, and the average reading for the background sensor(s), and use these values in a conventional subtraction and threshold comparison. Although this may be suitable in some implementations, for binary result outputs, it may not be optimal in the cases of channeling, as it has been found that the low test line values tend to suppress the average more than the high test line values raise it.

A more accurate and sensitive binary test result may be generated by instead separately subtracting each background sensor reading from each test line sensor reading, compare each to a threshold to produce a separate binary YES/NO result, and then output a YES result if 50% or more of the individual determinations is YES. To further reduce false positives, the averages may be subtracted and compared to a second threshold lower than the first threshold (e.g. 75% of the first threshold), and YES result output only if 50% or more of the individual subtractions are greater than the first threshold, and the average computation is greater than the second threshold. With two test line sensors and two background sensors, a sensor reading is acquired for each sensor, and a sum (equivalently an average) and a difference for each pair of sensor readings can be obtained. This is sixteen values that can be used to generate a binary validity determination and a binary test result for a valid test.

It may also be noted that this relatively rich source of data regarding test line development can be obtained with only four photodetectors, which is cost effective for a disposable device, which is one especially advantageous application of the principles described above.

In one specific implementation, the above described principles can be applied to a disposable pregnancy test device. Such devices should be small and as inexpensive as possible. For a device such as pictured in FIGS. 1A and 1B, the housing containing all the components may be less than 20 cm long, less than 4 cm wide, and less than 2 cm thick. The test strip in such a device may be 4-8 mm wide for example. These implementations use very small and inexpensive photodetectors of photodiode or phototransistor design with dimensions of only 1 or 2 mm on a side. These devices generally have wide viewing angles of half sensitivity typically of ±50-60 degrees, and are placed with their input window about 0.5 to 2 mm away from the test strip. No focusing optics or lenses are typically used. Therefore, with a 60 degree viewing angle and a 1 mm distance between the photodetector and the strip surface, the photodetector is sensitive to reflected light from about a 3 or 4 mm diameter circular area of the test region centered at the center of the strip.

When detecting the presence of pregnant condition, these test devices generally detect the analyte hCG in a urine sample. For a pregnant woman after 6 weeks from the last menstrual period, the hCG level in urine is very high, generally many thousands of mIU/ml, which is easily detectable with a single photodetector over the test region. Prior to this point, the hCG level increases dramatically starting at about 3 weeks following the last menstrual period. Because early pregnancy detection is extremely important, it is highly desirable to successfully detect low levels of hCG, such as 3 mIU/ml, which is a level typically attained between 3 and 4 weeks following the last menstrual period by a pregnant woman.

Especially when detecting these low levels, channeling of the fluid flow in the strip during the test can produce significant variations in test line development. A single detector will still work successfully if the channeling pushes the reagents to the center of the strip, but reagents pushed toward the edges of the strip can be missed because the viewed are of the photodetector is concentrated in the center of the strip. Increasing the distance between the strip and the detector may increase the viewed area, but the signal intensity will decrease. Tests performed by the applicant with test samples containing 3 mIU/ml hCG on conventional test strips have found that depending on the area of the test region being analyzed, a test performed with a sample containing 3 mIU/ml hCG produces test results indicating anywhere from 0 to 6 mIU/ml concentration for the test sample.

If one additional detector is provided for the test region, channeling toward the edges will not significantly interfere with successful detection low levels of hCG. For example, for the implementation illustrated in FIG. 3, the test strip 210 may be 6 mm wide, and two photodetectors 310 and 312 with 60 degree viewing angles may be placed with their light sensitive surfaces about 1 mm above the strip surface, and positioned along the width of the strip about 1 mm on either side of the center of the strip. With this configuration, coverage of the entire strip width is provided by the overlapping viewed areas of the two photodetectors, increasing the sensitivity of the test to low hCG levels in the presence of channeling. No optics or lenses are needed, no increase in size is needed, and the only cost increase over a conventional device is one additional photodetector. Very simple processing could be performed, involving simply summing or averaging the data from the two photodetectors 310 and 312.

It will be appreciated that 3 or 4 photodetectors could also be used positioned across the width of the strip, depending on the strip width, the viewing angles of the photodetectors, and the distance between the photodetectors and the strip surface.

Advantageous implementations may thus be created when exactly two, exactly three, or exactly four photodetectors are used to view the test region of the strip, each having lengths, widths, and heights less than 3 mm, and that are placed across the width of the strip with their light sensitive surfaces less than 2 mm from the surface of the test region of the strip. The photodetectors in these implementations may have a viewing angle of half sensitivity of ±40-80 degrees. Generally, exactly two photodetectors positioned to view the test region of the strip is advantageous for cost purposes, given that coverage of the complete strip width can still be provided. Also, it is advantageous for cost and size purposes when no lenses or other optics are provided between the test strip and the light sensitive surfaces of the photodetectors.

Figure 8:
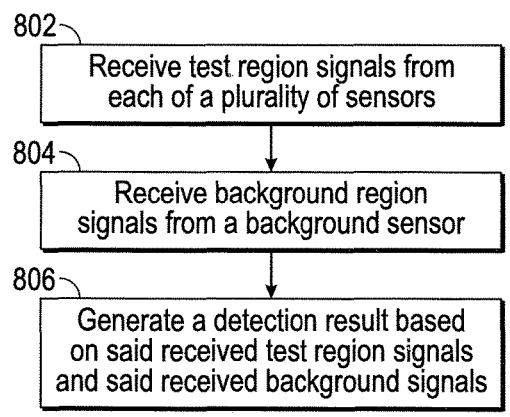
FIG. 8 is a flow diagram of a method of detecting a monitored analyte.

FIG. 8 is a flow diagram of a method of detecting a monitored analyte. The method shown in FIG. 8 may be implemented in one or more of the devices described such as shown in FIGS. 1-4 or by the processor included in the circuit shown in FIG. 6.

At node 802, test region signals are received. The test region signals indicate a quantity of light reflected from a test region included on a test strip from each of a first plurality of sensors. At node 804, background signals are received. The background signals indicate a quantity of light reflected from a background region included on said test strip from a background sensor. At node 806, a detection result is generated based on said received test region signals and said received background signals.

It will be appreciated that the above described system could be used to detect analytes other than hormones, with especially advantageous application in any environment where samples are collected, and the diagnostic test may be interpreted according to a photosensitive reading. For example, variation of the monitored analyte may be used to indicate an onset of menopause (e.g., natural menopause, perimenopause, induced menopause, premature menopause, or post menopause) or ovarian reserve for the individual. In an implementation, variation of a monitored analyte such as progesterone may be used to indicate an onset of an abnormal pregnancy (e.g., failed implantation, ectopic pregnancy) for the individual. In an example progesterone implementation, a normal pregnancy is detected if the progesterone level is greater than the threshold value while levels equal to or less than the threshold indicate an abnormal or failing pregnancy. The detection method or device may be included in a test kit such as an ovulation detector test kit sensing luteinizing hormone (LH) in urine samples from an individual.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various operations of methods described above may be performed by any suitable means capable of performing the operations, such as various hardware and/or software component(s), circuits, and/or module(s). Generally, any operations illustrated in the Figures may be performed by corresponding functional means capable of performing the operations.

The various illustrative logical blocks, modules and circuits described in connection with the present disclosure may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Thus, in some aspects computer readable medium may comprise non-transitory computer readable medium (e.g., tangible media). In addition, in some aspects computer readable medium may comprise transitory computer readable medium (e.g., a signal). Combinations of the above should also be included within the scope of computer-readable media.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Software, instructions, or data may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a device as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a device can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

While the foregoing is directed to aspects of the present disclosure, other and further aspects of the disclosure may be devised without departing from the basic scope thereof, and the scope thereof is determined by the claims that follow.

What is claimed is:

1. A disposable analyte detection device comprising:
 a receiving member configured to receive a test strip comprising a test region and a background region laterally displaced along the length of said test strip;
 a first plurality of sensors placed such that said first plurality of sensors are located above said test region once said test strip is received;
 at least one background sensor placed such that said background sensor is located above said background region once said test strip is received; and a light source placed such that said light source illuminates said test region and said background region once said test strip is received; and a processor programmed to:

receive test region signals indicating a quantity of light reflected from said test region from each of said first plurality of sensors;

receive background signals indicating a quantity of light reflected from said background region from said background sensor; and generate a detection result based at least in part on a comparison of at least some of said received test region signals with at least some of said received background signals, wherein the processor is programmed to receive test region signals and background signals over a period of time, and wherein generating the detection result comprises, for a point during said period of time, combining a test region signal from one of said first plurality of sensors with a background signal and comparing said combination to a threshold.

2. The device of claim 1, wherein said first plurality of sensors includes two or three sensors.

3. The device of claim 1, further comprising a second background sensor, said second background sensor also placed such that said second background sensor is located above said background region once said test strip is received, wherein said received background signals include signals from said second background sensor, and wherein generating said detection result comprises combining said test region signal from one of said first plurality of sensors with one of a background signal received from one of said background sensor or said second background sensor and comparing said combination to said threshold.

4. The device of claim 3, wherein the first plurality of sensors include a left test region sensor and a right test region sensor, and wherein the device includes a left background region sensor and a right background region sensor.

5. The device of claim 4, wherein the processor is programmed to generate said detection result by:

subtracting said left test region sensor value from said left background region sensor value;

subtracting said right test region sensor value from said right background region sensor value; and comparing said results to said threshold.

6. The device of claim 4, wherein the processor is programmed to generate said detection result by:

subtracting said left test region sensor value from said right background region sensor value;

subtracting said right test region sensor value from said left background region sensor value; and comparing said results to said threshold.

7. The device of claim 1, wherein at least one of said first plurality of sensors and said at least one background sensor include a photodetector.

8. A method of detecting an analyte, the method comprising:

receiving, via a receiving member, a test strip comprising a test region and a background region laterally displaced along the length of said test strip;

illuminating, via a light source, said test region and said background region;

receiving, via a processor, test region signals indicating a quantity of light reflected from said test region included on the test strip from each of a first plurality of sensors;

receiving, via said processor, background signals indicating a quantity of light reflected from said background region included on said test strip from a background sensor; and generating, via said processor, a detection result based on said received test region signals and said received background signals, wherein receiving said test region signals and said background signals occurs over a period of time, and wherein generating the detection result comprises, for a point during said period of time, combining a test region signal from one of said first plurality of sensors with a background signal and comparing said combination to a threshold.

9. The method of claim 8, wherein receiving said test region signals comprises receiving test region signals from two or three sensors.

10. The method of claim 8, wherein receiving said background signals further comprises receiving background signals from a second background sensor, and wherein generating said detection result comprises combining said test region signal from one of said first plurality of sensors with one of a background signal received from one of said background sensor or said second background sensor and comparing said combination to said threshold.

11. The method of claim 10, wherein the first plurality of sensors include a left test region sensor and a right test region sensor, and wherein the device includes a left background region sensor and a right background region sensor.

12. The method of claim 11, wherein generating said detection result comprises:

subtracting said left test region sensor value from said left background region sensor value;

subtracting said right test region sensor value from said right background region sensor value; and comparing said results to a threshold.

13. The method of claim 11, wherein generating said detection result comprises:

subtracting said left test region sensor value from said right background region sensor value;

subtracting said right test region sensor value from said left background region sensor value; and comparing said results to a threshold.

14. The method of claim 8, wherein receiving said test region signals from said first plurality of sensors and receiving said background signals from said at least one background sensor comprises receiving respective signals from photodetectors.

15. A disposable analyte detection device comprising:

means for receiving a test strip comprising a test region and a background region laterally displaced along the length of said test strip;

means for illuminating said test region and said background region once said test strip is received;

means for receiving test region signals indicating a quantity of light reflected from said test region included on said test strip from each of a first plurality of sensors;

means for receiving background signals indicating a quantity of light reflected from said background region included on said test strip from a background sensor; and means for generating a detection result based at least in part on a comparison of at least some of said received test region signals with at least some of said received background signals, wherein receiving said test region signals and said background signals occurs over a period of time, and wherein generating the detection result comprises, for a point during said period of time, combining a test region signal from one of said first plurality of sensors with a background signal and comparing said combination to a threshold.

* * * * *